United States Patent [19]

Ledley

[11] 4,450,478
[45] May 22, 1984

[54] DIGITAL FLUOROGRAPHIC METHOD AND SYSTEM

[75] Inventor: Robert S. Ledley, Silver Spring, Md.
[73] Assignee: Georgetown University, Washington, D.C.
[21] Appl. No.: 300,587
[22] Filed: Sep. 9, 1981
[51] Int. Cl.³ .............................................. H04N 7/18
[52] U.S. Cl. ...................... 358/111; 378/99; 364/414
[58] Field of Search ................ 358/111; 378/99, 302, 378/303; 364/515, 415, 414, 416

[56] References Cited

U.S. PATENT DOCUMENTS

| | | | |
|---|---|---|---|
| 3,854,049 | 12/1974 | Mistretta et al. | 250/402 |
| 3,894,181 | 7/1975 | Mistretta et al. | 178/6.8 |
| 3,974,386 | 8/1976 | Mistretta et al. | 250/402 |
| 4,172,978 | 10/1979 | Houmsfield et al. | 364/414 |
| 4,204,225 | 11/1980 | Mistretta | 358/111 |
| 4,204,226 | 5/1980 | Mistretta et al. | 358/111 |
| 4,229,797 | 10/1980 | Ledley | 364/515 |

OTHER PUBLICATIONS

M. M. Frost et al., "Digital Acquisition System for Photo-Electronic Radiology-A Performance Overview", SPIE, vol. 233, Application of Optical Instrumentation in Medicine VIII, (1980).

Ernest L. Hall, *Computer Image Processing and Recognition*, New York: Academic Press, (1979), pp. 33 and 200–214 and 263–265.

Robert S. Ledley et al., "TEXAC: A Special Purpose Picture Processing Texture Analysis Computer", Proc. 15th IEEE Comp. Soc. Int. Conf., 9/77, Wash DC
R. S. Ledley et al., "TEXAC Pattern Recognition Computer", Dept. of Phys. and Biophysics, GU Medical School, Wash., DC, (1978).

*Primary Examiner*—John C. Martin
*Assistant Examiner*—Edward L. Coles
*Attorney, Agent, or Firm*—Oblon, Fisher, Spivak, McClelland & Maier

[57] ABSTRACT

A digital fluorographic method and system calls for digitizing and storing first and second x-ray picture information derived prior to and after, respectively, injection of a contrast medium into the subject. The first and second x-ray picture information are digitized, stored and processed to develop first and second processed picture data, respectively, and the first and second processed picture data are subtractively combined to produce picture data corresponding to a pictorial representation of differences between the x-ray picture information prior to and after, respectively, the injection of the contrast medium. The method and system call for various combinations of the following operations: averaging one or both of the x-ray picture data; convolution of the picture data derived prior to the injection of the contrast medium; pre-enhancement of one or both of the x-ray picture data; and post-enhancement of the picture data corresponding to the pictorial representation of the differences between the x-ray pictures prior to and after, respectively, the injection of the contrast medium. The inventive system includes a plurality of storage units and display units, in conjunction with an image processor, for rapidly operating on (whole-picture processing) the various x-ray picture data provided to the system.

| AVERAGE A OR B OR BOTH | CONVOLVE A | PRE-ENHANCE A OR B OR BOTH | DIFFERENCE B-A | POST-ENHANCE |
|---|---|---|---|---|
| | | | X | |
| | | | X | X |
| | | X | X | |
| | | X | X | X |
| | X | | X | |
| | X | | X | X |
| | X | (B) | X | |
| | X | (B) | X | X |
| X | | | X | |
| X | | | X | X |
| X | | X | X | |
| X | | X | X | X |
| X | X | | X | |
| X | X | | X | X |
| X | X | (B) | X | |
| X | X | (B) | X | X |

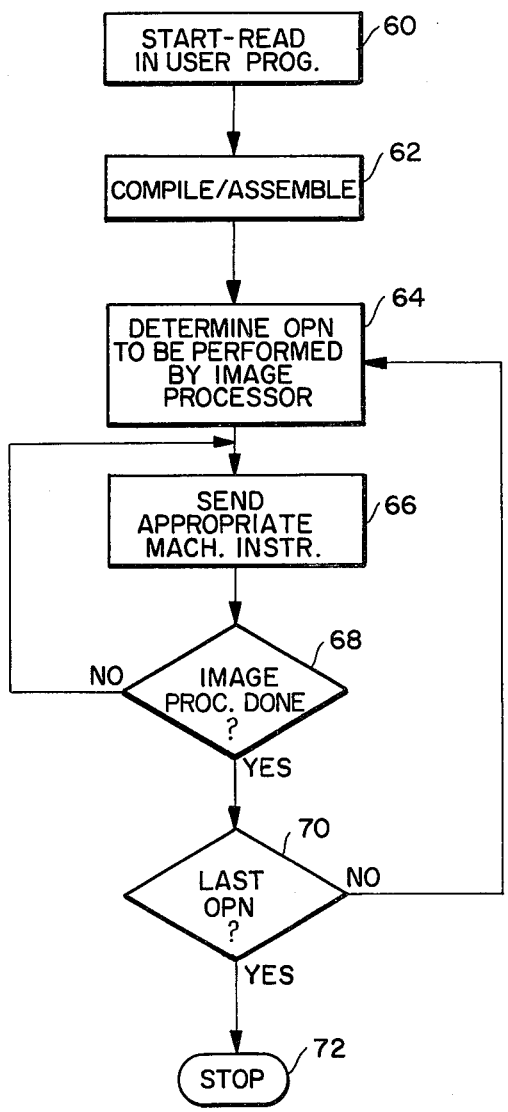

DIGITAL FLUOROGRAPHIC METHOD AND SYSTEM

BACKGROUND OF THE INVENTION

1. Field of the Invention

The present invention relates to a digital fluorographic method and system, and, more particularly, to a method and system which calls for the digitization and storage of first and second x-ray picture data derived prior to and after, respectively, injection of a contrast medium into a subject. The method and system of the invention utilize various techniques, and combinations of techniques, to develop a pictorial representation of the differences between the x-ray picture prior to injection of the contrast medium and the x-ray picture after injection of the contrast medium.

2. Description of the Prior Art

Many of the most important potential applications of computer picture processing, particularly in the field of clinical x-rays and fluorography, have not yet been successfully carried out on a feasible basis because of one fundamental difficulty. Applications, such as the analysis of fluoroscopic images, require an evaluation of the "texture" of an object before and after the injection of a contrast medium. Some work has been done in this area in an effort to improve real-time digital x-ray imaging. Typical of such efforts are the following U.S. Pat. Nos. 3,854,049; 3,894,181; 3,974,386; 4,204,225; and 4,204,226.

Considering U.S. Pat. No. 4,204,225, that patent discloses a real-time digital x-ray subtraction imaging method and apparatus having application in conducting diagnostic x-ray studies of humans and animals, and, in particular, in visualizing the cardiovascular system, including the heart and blood vessels which are of interest. Other applications for such imaging methods and apparatus include visualizing the motion of the heart in real time, displaying the circulation of the blood in the arteries and veins associated with the heart, and conducting x-ray studies of the abdomen and brain.

Such prior art techniques have been directed to achievement of improved television difference images, in which the blood vessels (for example) are shown with greatly enhanced visibility, while image elements due to bone and soft tissue are largely eliminated. Such methods and apparatus typically employ subtraction techniques for accomplishing this purpose. As a result of such subtraction techniques, television difference images are produced. In such television difference images, the visibility of an x-ray contrast medium (injected into the subject) is enhanced.

Despite such techniques of the prior art, however, the quality of the resulting x-ray images is still in need of substantial improvement. This is a result of the fact that techniques of the prior art, such as disclosed in the prior patents mentioned above, have merely employed relatively simplistic known techniques, such as enhancement, integration and subtraction. For example, U.S. Pat. No. 3,854,049 merely performs simple image subtraction of two x-ray images. U.S. Pat. No. 3,894,181 merely performs two complementary subtractions of two images, and integrates the differential portions thereof while subtractively combining the nondifferential portions thereof. U.S. Pat. No. 3,974,386 utilizes a relatively simple technique of combining first, second and third x-ray images, by means of which technique the first and third images are averaged, and the resulting average is subtractively combined with the second image. Finally, U.S. Pat. Nos. 4,204,225 and 4,204,226 also utilize a relatively simplistic technique, involving the conversion of an x-ray image into a series of television fields comprising trains of analog video signals, converting the analog video signals into digital form, integrating the resulting digital signals over a series of successive time intervals, and performing a series of subtractions between each set of integrated video signals and the preceding set of integrated video signals to produce a series of successive digital difference video signals which are then converted to analog form and displayed. Prior to conversion to analog form, conventional enhancement of the digital difference video signals can, according to the latter patents, be carried out. In addition, according to U.S. Pat. No. 4,204,225, a contrast medium can be injected prior to the subtraction process and with such timing that the contrast medium appears in the x-ray image subsequent to the time interval over which the digital video signals were integrated.

As is clear from the preceding discussion, prior art practitioners have only employed such procedures as integration, enhancement and subtraction in their quest for improved subtraction or difference imaging techniques. As a result, such techniques are still lacking in quality of the difference image resulting therefrom. In addition, the prior art technology, in general, and the aforementioned patents, in particular, have not provided an integrated system for carrying out difference imaging in as highly an efficient manner as is possible, utilizing current technology, and have not provided an integrated system wherein the system operator can simultaneously view the original x-ray picture (prior to injection of the contrast medium), the subsequent x-ray picture (subsequent to injection of the contrast medium), the difference image resulting from a subtractive combination of the original and subsequent x-ray images, and an enhanced version of the resulting difference image. The provision of such an integrated system for simultaneously displaying the aforementioned images would represent a significant improvement over the prior art, and would have substantial and obvious advantages to the medical diagnostician and to the users of such a system.

SUMMARY OF THE INVENTION

According to the present invention, there is provided a digital fluorographic method and system, and, more particularly, a system and method for providing a pictorial representation of the differences between an x-ray picture prior to injection of a contrast medium and a further x-ray picture after injection of the contrast medium.

More specifically, the digital fluorographic method generally calls for the obtaining of an x-ray picture of a subject prior to injection of the contrast medium, the injection of a contrast medium into the subject, and the obtaining of a further x-ray picture after the injection of the contrast medium. The resulting x-ray pictures are digitized and stored in separate memories in the associated system, and can be separately whole-picture processed by a digital image processor so as to develop corresponding processed picture data. The resulting processed picture data are then subtractively combined to produce picture data corresponding to a pictorial representation of differences between the x-ray picture prior to injection of the contrast medium and the further x-ray picture after injection of the contrast medium.

As indicated below, the digital fluorographic method and system of the present invention employs sophisticated techniques for improving the quality of the picture data corresponding to the x-ray pictures prior to, and subsequent to, the injection of the contrast medium. Such techniques include, but are not limited to, averaging, convolution, pre-enhancement, subtraction, and post-enhancement. These techniques may be employed in various combinations, in accordance with the particular fluorographic application being carried out. These techniques will be described in further detail below.

The digital fluorographic system of the present invention receives and digitizes the analog video signals corresponding to the x-ray pictures prior to, and subsequent to, injection of the contrast medium. The digital x-ray picture information prior to injection is stored in one memory, and the digital x-ray picture information subsequent to injection is stored in another memory. As mentioned above, further memories are provided; for example, one additional memory is provided for holding the digital difference image data resulting from the subtractive combination of the first and second picture information, while a further memory can be provided for holding further data resulting from enhancement of the difference image data stored in the first additional memory. As also indicated above, a plurality of display units, one for each memory if desired, can be provided so as to provide the diagnostician with the ability to simultaneously view the pre-injection x-ray picture, the post-injection x-ray picture, the difference image, and the enhanced difference image.

Whereas a single processor can be employed, in the inventive system, for carrying out the storage functions (via a plurality of memories), the processing functions (by means of which averaging, convolution, enhancement, etc. are carried out), and the "housekeeping" functions for controlling the overall operation of the system, a preferred embodiment of the invention involves the provision of a digital image processor or whole-picture processor (such as disclosed in U.S. Pat. No. 4,229,797) for the image storage and image processing functions, while relegating the "housekeeping" and control functions to a general-purpose host computer.

Therefore, it is an object of the present invention to provide a digital fluorographic method and system which receives, digitizes, processes and subtractively combines x-ray picture information obtained prior to injection of a contrast medium and x-ray picture information obtained subsequent to injection of a contrast medium.

It is an additional object of the present invention to provide a digital fluorographic method and system which, in processing the pre-injection and post-injection x-ray picture data, employs sophisticated data processing techniques, including, but not limited to, averaging, convolution, pre-enhancement, subtraction, and post-enhancement.

It is an additional object of the present invention to provide a digital fluorographic method and system, wherein pre-injection and post-injection x-ray picture data are separately stored in an image memory, and can be simultaneously viewed on separate displays.

It is an additional object of the present invention to provide a digital fluorographic method and system, wherein an additional memory is provided for holding the results of subtractive combination of the pre-injection and post-injection x-ray picture information, as well as a separate display unit for separately displaying (simultaneously with display of the pre-injection and post-injection picture information) a difference image constituting a pictorial representation of the differences between the successive x-ray pictures taken of the subject prior to and after injection of the contrast medium.

It is an additional object of the present invention to provide a digital fluorographic method and system, wherein the digital information resulting from the subtractive combination of pre-injection and post-injection x-ray information is subject to post-enhancement, and the resulting enhanced data is separately stored and separately displayed for simultaneous viewing with the pre-injection and post-injection x-ray information, as well as with the difference image.

The above and other objects that will hereinafter appear, and the nature of the invention, will be more clearly understood by reference to the following description, the appended claims, and the accompanying drawings.

BRIEF DESCRIPTION OF DRAWINGS

FIG. 5 is a flowchart of operations performed by the host digital computer operating in conjunction with the digital fluorographic system of the present invention.

DETAILED DESCRIPTION

Figures 1, 3:
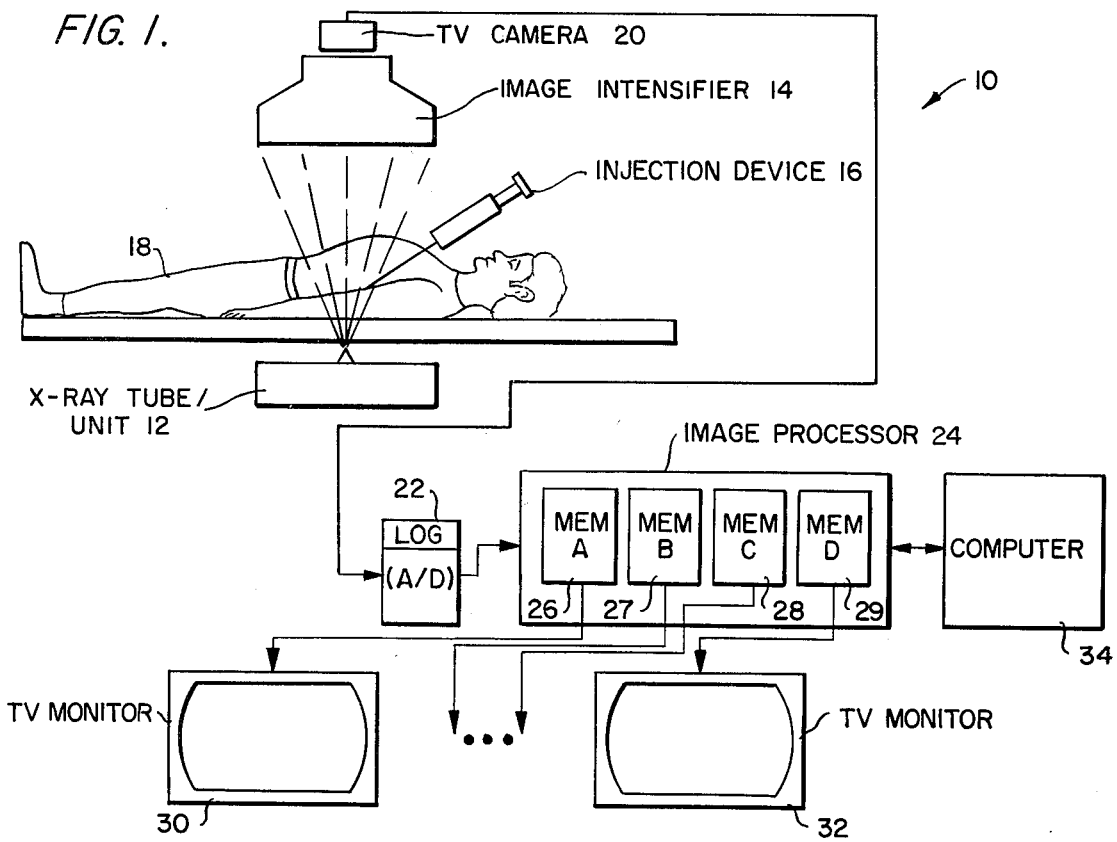
FIG. 1 is a diagrammatic representation of the digital fluorographic method and system employed in combination with an x-ray system, an image intensifier system, a television system, and a contrast medium injection device.
FIG. 3 is a table illustrating various processing techniques (averaging, convolution, pre-enhancement, subtraction, and post-enhancement) which are employed in accordance with the method and system of the present invention.

The present invention will now more fully be described, with reference to FIG. 1, which is a diagrammatic representation of the digital fluorographic method and system of the present invention, as employed in conjunction with an x-ray tube system, an image intensifier system, a television system, and an injection device.

Referring to FIG. 1, the digital fluorographic system 10 is employed in conjunction with a conventional x-ray system 12, image intensifier system 14, and injection device 16 (for injecting contrast medium into the subject 18). The digital fluorographic system further comprises a TV camera system 20, analog-to-digital converter (ADC) 22, image processor 24 (having memories 26–29), display units 30 and 32 (additional display units can, of course, be provided), and a digital computer 34.

In operation, the x-ray tube 12 makes an x-ray exposure of the subject 18, the transmitted x-rays being intercepted by the image intensifier 14. The image intensifier 14 is viewed by a TV camera 20, and the resulting analog video signal is processed (e.g., amplified, logged, etc.) and provided to ADC 22 wherein it is digitized. The resulting digitized picture, which is typically divided into television images (as is well-known in the television art), is then transmitted to a digital image memory (e.g., memory (A) 26). As will be discussed in further detail below, the memory 26, as well as the other memories 27–29, are solid-state memories which, as is well-known in the art, when properly designed, can provide (with suitable digital-to-analog conversion) analog video signals for driving a conventional television monitor (such as TV monitor 30) so as to provide a constant display. In the latter manner, a constant display, on monitor 30, of the pre-injection x-ray of the subject 18 is obtained.

Once a satisfactory x-ray picture of the subject 18 is obtained, the injection device 16 may be employed, in accordance with conventional clinical techniques, to inject a contrast medium into the body of the subject 18. It is understood that, if an "energy difference picture" is desired, the x-ray energy can be varied accordingly. This will result in modification of the x-ray picture generated on the image intensifier 14 and camera 20, and the resulting post-injection picture data, after digitization in ADC 22, is provided to the image processor 24, wherein it is stored in memory (B) 27. As is the case with memory 26, the information stored in memory 27 can also be displayed on a TV monitor (not shown).

As mentioned previously, the image processor 24 is a digital image processor, such as is disclosed in U.S. Pat. No. 4,229,797. It is this image processor 24 which performs the image processing techniques so as to whole-picture process each of the displayed images (that is, each of the x-ray pictures stored in memories 26 and 27 and displayed on corresponding monitors) in real time and, thus, derives a difference image which is then stored in memory 28 and displayed on a corresponding monitor. As disclosed in the latter U.S. patent, the image processor 24 would typically include a video processor (not shown) for performing the image processing, and a video crossbar switch (also not shown) for performing routing operations for routing data to and from the various memories and the video processor, the memories 26–29, and various transfer units (not shown) for gating data into and out of the memories 26–29 and TV monitors 30 and 32.

As also described in the latter patent, the TV camera 20 operates in synchronization with the image processor 24 (such synchronization being known to those of skill in the art) to scan the image intensifier 14, and to relay the resulting analog video signals to the ADC 22, which performs digital conversion, the resulting digital data being provided to the image processor 24 and, via the video crossbar switch (not shown) therein, to a respective one of the memories (for example, memory 26). This provides the system with the capability of operator monitoring of the pre-injection x-ray picture. Once the contrast medium is injected into the subject 18, the system can be appropriately controlled by the operator (via conventional operator controls) for directing the video crossbar switch to route the digital x-ray information corresponding to the post-injection x-ray picture into a different memory (for example, memory 27). Thus, the system again provides the capability of operator monitoring of the image, this time the x-ray image subsequent to injection.

Then, the operator, by conventional operator controls (as taught in the art, especially in view of the aforementioned U.S. patent), instructs the system to perform image processing of the data contained in memories 26 and/or 27, followed by subtractive combination of the resulting processed data to form difference image data, which is then stored in memory 28. In a preferred embodiment, this difference image data can also be processed (for example, post-enhanced), with the resulting processed data stored in memory 29. As previously mentioned, both the pre-enhanced and post-enhanced data stored in memories 28 and 29, respectively, can be displayed on corresponding TV monitors.

As indicated above, each of memories 26–29 is provided, at its output, with a corresponding transfer gate, such transfer gates being enabled by conventional control signals provided by the video processor (also not shown, but disclosed in U.S. Pat. No. 4,229,797) in image processor 24 in response to operator input controls. As a result of enablement of these transfer gates, previously stored information in memories 26–29 can be provided to the video crossbar switch (not shown) for further provision to the video processor (when the video processor is to be utilized for image processing). In addition, the transfer gates, when appropriately enabled, can provide the stored information from memories 26–29, via appropriate digital-to-analog converters, to display units (such as TV monitors 30 and 32), thus, achieving display of the contents of each of memories 26–29.

As also previously indicated above, memories 26–29 are conventional high-speed solid-state memory units, for example, MOS (metal oxide semiconductor) memories. As is known in the art, such memories can be provided with timing control units for continuously gating stored information synchronously at high (TV scan) rates with appropriate intervals for horizontal and vertical retrace, just as in a TV camera or monitor.

Figure 2:
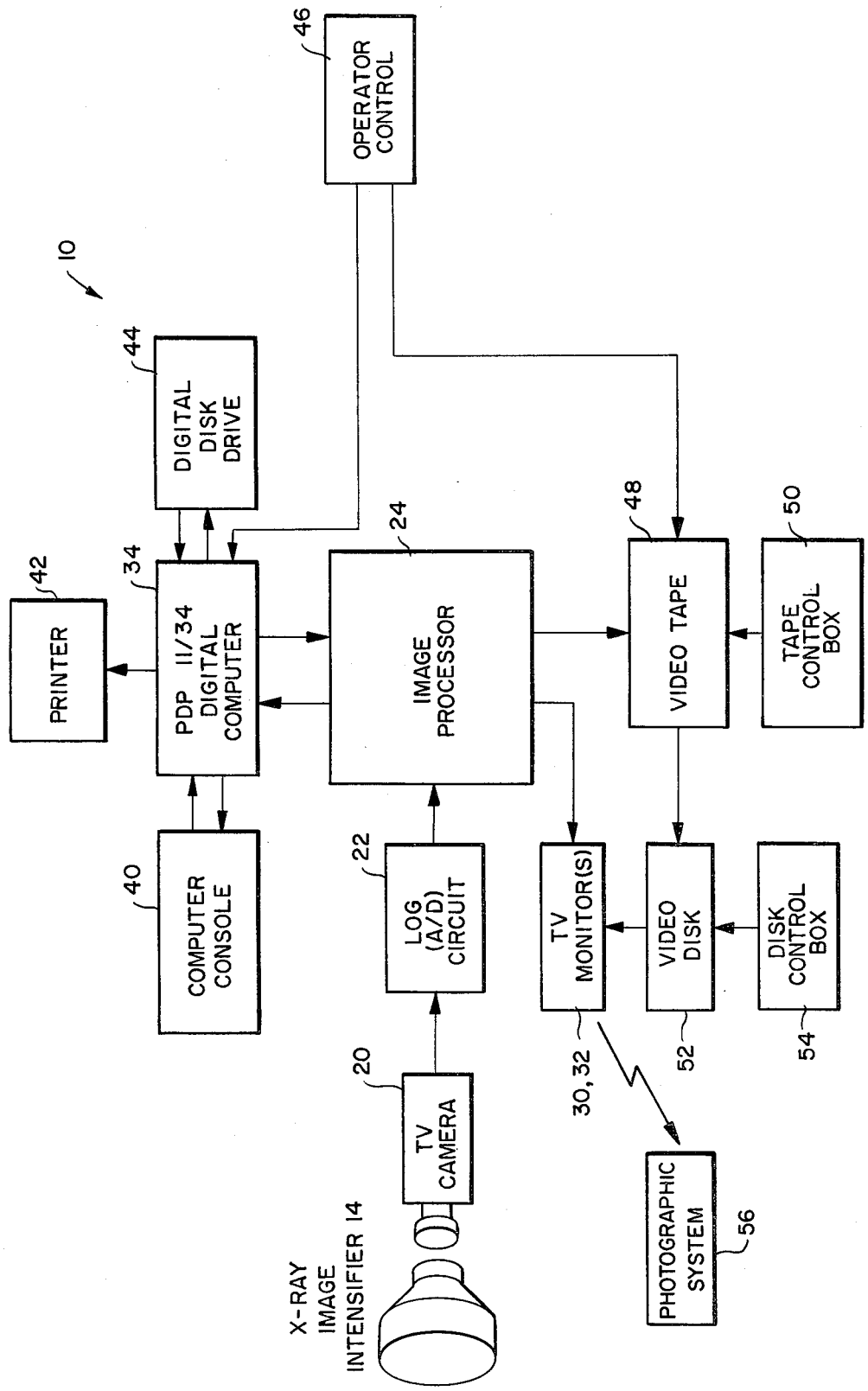
FIG. 2 is a block diagram of the digital fluorographic system of the present invention.

FIG. 2 is a detailed block diagram of the digital fluorographic system 10 of FIG. 1.

As seen therein, the system includes the x-ray image intensifier 14, the TV camera 20, the ADC 22, the image processor 24, the TV monitor or monitors 30, 32, and the digital computer 34. In addition, as seen in FIG. 2, the system can include other conventional peripheral units normally associated with digital computer systems, such as computer console 40, printer 42, and digital disk drive 44. In addition, an operator control box 46, video tape unit 48, videotape control box 50, video disk 52, video disk control box 54, and photographic system 56 are included.

In operation, the preferred embodiment of the system of the present invention provides various means for storing digital x-ray picture information once it is received from the image intensifier 14 and TV camera 20, via the ADC 22. That is to say, once such information is received, the image processor 24 can store such information, via computer 34, on the digital disk 44. In addition, the picture data can be transferred from the image processor 24 to the video tape 48 or video disk 52, and can be subsequently displayed on TV monitor(s) 30, 32.

The arrangement of and relationship between image processor 24 and digital computer 34 is well-known to those of skill in the art. As indicated in aforementioned U.S. Pat. No. 4,229,797, an image processor, such as image processor 24, operates in conjunction with a host computer, such as digital computer 34, with the interface between the image processor 24 and digital computer 34 being a conventional bus-type interface. The use of a dedicated image processor 24 provides the system with the capability of considering all picture elements as one "picture-word", and, once instructed by the host digital computer 34 to perform an operation, the image processor 24 operates on the whole picture independent of the host computer 34. It can do this at a very high speed, taking (for example) 1/30 of a second (the standard TV frame rate). Moreover, the image processor 24 can be specially tailored to execute uniquely designed instructions (provided by the computer 34 to the processor 24) so as to perform such operations as are typical of the sophisticated image processing techniques, to be discussed below. Moreover, such image processing techniques, despite their sophistication, can be performed with respect to a whole picture in a very rapid and efficient manner.

The TV monitor(s) 30, 32 provide an image which can be, if desired, reproduced by conventional photographic techniques, using the photographic system 56, the latter being (for example) an imaging or photographic system manufactured under Model No. 649 by Dunn Instrument Co., or similar device.

FIG. 3 is a table which illustrates the various combinations of picture processing techniques, which can be performed with respect to the pre-injection x-ray picture (A) and post-injection x-ray picture (B). As indicated in the table of FIG. 3, various options are presented in accordance with the digital fluorographic method and system of the present invention, including: (1) averaging A or B, or both; (2) convolving A; (3) pre-enhancing A or B, or both; (4) subtractively combining A and B (as previously processed); and (5) post-enhancing the results of the subtractive combination in (4).

The technique of averaging A or B, or both, involves taking a frame A1 of picture A in conjunction with another frame A2 of picture A, and developing a numerical average (the sum divided by two) of these two elements so as to effectively replace the two points by the numerical average. If A is to be averaged, the latter technique is carried out for each respective corresponding point in picture A and, similarly, if picture B is to be averaged, the numerical averaging technique is carried out for corresponding points in picture B.

The procedure of convolving A amounts to having, for each point of picture A, a grey scale value, and replacing the value of that point by some function of all of the points in a suitably defined neighborhood of points associated with the given point. The technique of convolving a given picture, as implemented in the present invention, need not be discussed further, since convolution techniques are well-known in the art, and are discussed in the references and literature (see, for example, *Computer Image Processing and Recognition*, by Ernest L. Hall, New York: Academic Press, 1979, pages 33 and 263 ff.).

The technique of enhancement is a technique known in picture processing technology, whereby the contrast between neighboring areas of a picture having different contrast is increased, while the total range of contrast of the image is decreased. In connection with the implementation of the present invention, any suitably defined edge-enhancing algorithm may be employed. Such edge-enhancing algorithms are also well-known in the art (see, for example, the aforementioned publication by Ernest L. Hall, pages 200 ff.).

In contrast to prior art practitioners, it has been found that, by implementing the digital fluorographic method and system of the present invention, much better image processing results can be obtained. For example, in contrast to the previously mentioned prior art patents, which merely teach the use of integration techniques, subtraction techniques, and post-enhancement techniques, one embodiment of the present invention calls for pre-enhancement of picture A or picture B (the pre-injection and post-injection x-ray pictures, respectively), or both, and much improved results have been obtained. Similarly, improved results have been obtained by employing, in a further embodiment of the present invention, convolution of picture A (the pre-injection picture), with or without pre-enhancement of picture B.

In fluorographic arrangements of the prior art, the x-ray picture results are considerably reduced in quality if the patient moves after the contrast material is injected. Such movement by the patient results in a "highlighting" effect, and examination of the resulting x-ray may give erroneous information. In accordance with the present invention, this disadvantage stemming from patient movement is eliminated by employment of convolution of picture A (the pre-injection picture), and slight patient movement will not result in such an artifact (the highlighting effect) previously discussed. In addition, convolution of picture A reduces "fuzziness" experienced at the borders between contrasting elements of the x-ray picture.

Finally, use of pre-enhancement and post-enhancement techniques, in accordance with the present invention, improves the contrast between bodily organs or elements into which the contrast medium has been injected, on the one hand, and those organs or elements which have not received the contrast medium, on the other hand. The result of such enhancement is improved clarity, resolution and definition in x-ray pictures, and resulting improved clarity in difference images resulting from subtractive combination of pre-injection and post-injection pictures.

Figure 4:
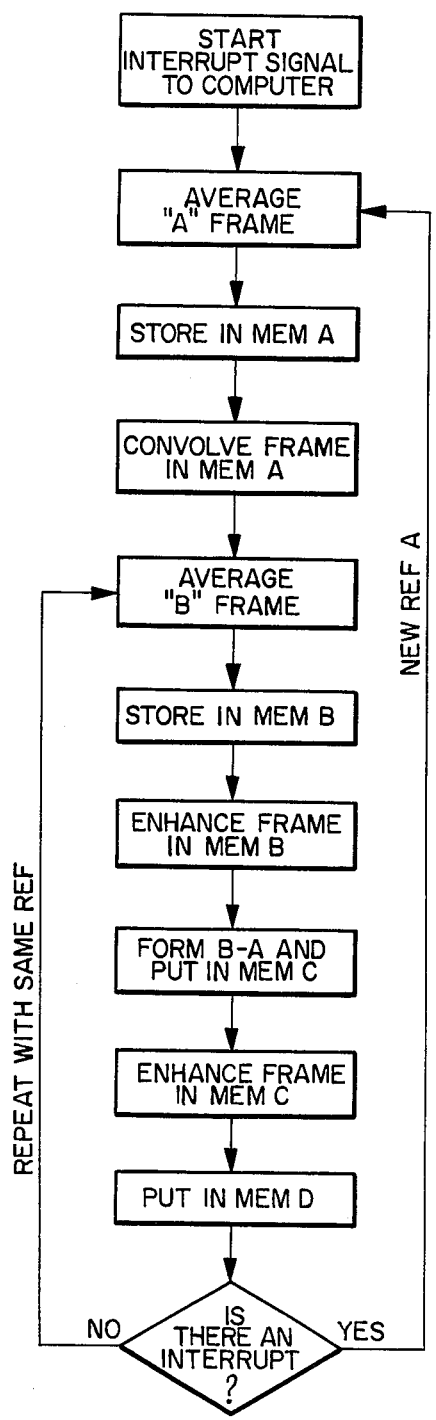
FIG. 4 is a flowchart of the operations performed by the image processor of FIG. 2.

FIG. 4 is a flowchart of a typical sequence of operations performed by the image processor 24 of FIGS. 1 and 2. Specifically, the operations represented by the flowchart of FIG. 4 correspond to the image processing operations appearing in the last line of the table of FIG. 3. Since the operations appearing in each block of the flowchart of FIG. 4 are self-explanatory, further description is not necessary.

FIG. 5 is a flowchart of operations performed by the computer 34 of FIGS. 1 and 2. As indicated in FIG. 5, the digital fluorographic system of the present invention is started (block 60) by operator control, as a result of which a user program is read in, typically from digital disk drive 44 of FIG. 2. The user program is compiled/assembled (block 62) to obtain machine-language instructions for subsequent provision to the image processor 24. In accordance with the user program, the computer 34 determines what operations are to be performed by the image processor 24 (block 64), and sends appropriate machine instructions to the image processor 24 (block 66). The computer 34 then waits for the image processor to be done with the present operation (block 68). So long as the present operation is being carried out, the computer 34 continues to send appropriate machine instructions (block 66) to the processor 24. Once the processor 24 has completed the operation, the computer 34 determines whether or not the operation was the final operation (block 70). If it was not the final operation, the computer 34 determines what further operation is to be performed by the image processor 24 (block 64); conversely, if it was the last operation, the computer 34 stops (block 72) until further actuation by the operator.

While preferred forms and arrangements have been shown in illustrating the invention, it is to be clearly understood that various changes in detail and arrangement may be made without departing from the spirit and scope of this disclosure.

What is claimed is:

1. A digital fluorographic method, comprising the steps of:
   (a) obtaining an x-ray picture of a subect, said x-ray picture comprising a plurality of frames;
   (b) digitizing and storing said x-ray picture as digital x-ray picture data divided into frames;
   (c) averaging and convolving a predetermined number of said frames of said digital x-ray picture data to develop first processed picture data and displaying by a first display means said first processed picture data;
   (d) injecting a contrast medium into the subject;
   (e) obtaining a further x-ray picture of the subject;
   (f) digitizing and storing said further x-ray picture as further digital x-ray picture data;
   (g) operating on said further digital x-ray picture data to develop second processed picture data and displaying by a second display means said second processed picture data; and
   (h) subtractively combining said first and second processed picture data to produce picture information corresponding to a pictorial representation of differences between said x-ray picture prior to injection of said contrast medium and said further x-ray picture after injection of said contrast medium and displaying by a third display means said pictorial representation of differences whereby there is a simultaneous display by said first, second and third display means.

2. The method of claim 1, wherein said further digital x-ray data is divided into frames, and step (g) comprises averaging said predetermined number of said frames of said further digital x-ray picture data.

3. The method of claim 1, wherein said further digital x-ray data is divided into frames, and step (g) comprises enhancing said predetermined number of said frames of said further digital x-ray picture data.

4. The method of any one of claims 1, 2 or 3 further comprising the step (i) of enhancing said picture information to obtain enhanced picture information corresponding to an enhanced pictorial representation of differences between said x-ray picture prior to injection of said contrast medium and said further x-ray picture after injection of said contrast medium.

5. A digital fluorographic method, comprising the steps of:
   (a) obtaining an x-ray picture of a subject;
   (b) digitizing and storing said x-ray picture as digital x-ray picture data divided into frames;
   (c) operating on said digital x-ray picture data including convolving a predetermined number of said frames to develop first processed picture data and displaying by a first display means said first processed picture data;
   (d) injecting a contrast medium into the subject;
   (e) obtaining a further x-ray picture of the subject, said further x-ray picture comprising a plurality of frames;
   (f) digitizing and storing said further x-ray picture as further digital x-ray picture data divided into frames;
   (g) averaging a predetermined number of frames of said further digital x-ray picture data to develop second processed picture data and displaying by a second display means said second processed picture data; and
   (h) subtractively combining said first and second processed picture data to produce picture information corresponding to a pictorial representation of differences between said x-ray picture prior to injection of said contrast medium and said further x-ray picture after injection of said contrast medium and displaying by a third display means said pictorial representation of differences whereby there is a simultaneous display of said first, second and third display means.

6. The method of claim 5, wherein step (g) further comprises enhancing said further digital x-ray picture data.

7. The method of claim 5, wherein step (c) comprises enhancing said digital x-ray picture data.

8. The method of any one of claims 5, 6 or 7, further comprising the step (i) of enhancing said picture information to obtain enhanced picture information corresponding to an enhanced pictorial representation of differences between said x-ray picture prior to injection of said contrast medium and said further x-ray picture after injection of said contrast medium.

9. A digital fluorographic method, comprising the steps of:
   (a) obtaining an x-ray picture of a subject;
   (b) digitizing and storing said x-ray picture as digital x-ray picture data;
   (c) convolving said digital x-ray picture data to develop processed picture data and displaying by a first display means said processed picture data;
   (d) injecting a contrast medium into the subject;
   (e) obtaining a further x-ray picture of the subject;
   (f) digitizing and storing said further x-ray picture as further digital x-ray picture data and displaying by a second display means said further x-ray picture data; and
   (g) subtractively combining said processed picture data and said further digital x-ray picture data to produce picture information corresponding to a pictorial representation of differences between said x-ray picture prior to injection of said contrast medium and said further x-ray picture after injection of said contrast medium and displaying by a third display means said pictorial representation of differences whereby there is a simultaneous display by said first, second and third display means.

10. The method of claim 9, wherein said further digital x-ray data is divided into frames, and comprising the step, between steps (f) and (g), of enhancing said predetermined number of said frames of said further digital x-ray picture data.

11. The method of any one of claims 9 or 10, further comprising the step (h) of enhancing said picture information to obtain enhanced picture information corresponding to an enhanced pictorial representation of differences between said x-ray picture prior to injection of said contrast medium and said further x-ray picture after injection of said contrast medium.

12. A digital fluorographic method, comprising the steps of:
   (a) obtaining an x-ray picture of a subject;
   (b) digitizing and storing said x-ray picture as digital x-ray picture data;
   (c) enhancing said digital x-ray picture data to develop processed picture data and displaying by a first display means said processed picture data;

(d) injecting a contrast medium into the subject;
(e) obtain a further x-ray picture of the subject;
(f) digitizing and storing said further x-ray picture as further digital x-ray picture data and displaying by a second display means said further x-ray picture data; and
(g) subtractively combining said processed picture data and said further digital x-ray picture data to produce picture information corresponding to a pictorial representation of differences between said x-ray picture prior to injection of said contrast medium and said further x-ray picture after injection of said contrast medium and displaying by a third display means said pictorial representation of differences whereby there is a simultaneous display by said first, second and third display means.

13. The method of claim 12, wherein said further digital x-ray data is divided into frames, and comprising the step, between steps (f) and (g), of enhancing said predetermined number of said frames of said further digital x-ray picture data.

14. The method of any one of claims 12 or 13, further comprising the step (h) of enhancing said picture information to obtain enhanced picture information corresponding to an enhanced pictorial representation of differences between said x-ray picture prior to injection of said contrast medium and said further x-ray picture after injection of said contrast medium.

15. A digital fluorographic method, comprising the steps of:
(a) obtaining an x-ray picture of a subject;
(b) digitizing and storing said x-ray picture as digital x-ray picture data and displaying by a first display means said digital x-ray picture data;
(c) injecting a contrast medium into the subject;
(d) obtaining a further x-ray picture of the subject;
(e) digitizing and storing said further x-ray picture as further digital x-ray picture data;
(f) enhancing said further digital x-ray picture data to develop processed picture data and displaying by a second display means said processed picture data; and
(g) subtractively combining said digital x-ray picture data and said processed picture data to produce picture information corresponding to a pictorial representation of differences between said x-ray picture prior to injection of said contrast medium and said further x-ray picture after injection of said contrast medium and displaying by a third display means said pictorial representation of differences whereby there is a simultaneous display by said first, second and third display means.

16. The method of claim 15, further comprising the step (h) of enhancing said picture information to obtain enhanced picture information corresponding to an enhanced pictorial representation of differences between said x-ray picture prior to injection of said contrast medium and said further x-ray picture after injection of said contrast medium.

17. A digital fluorographic system for obtaining a pictorial representation of differences between successive x-ray pictures taken of a subject prior to and after, respectively, injection of a contrast medium into the subject, said system comprising:

digitizing means for digitizing said x-ray picture taken prior to injection of said contrast medium to provide first digital x-ray picture data, and for digitizing said x-ray picture taken after injection of said contrast medium to provide second digital x-ray picture data, said first and second digital x-ray picture data having a plurality of frames;

first storage means for storing said first digital x-ray picture data;

second storage means for storing said second digital x-ray picture data;

first display means responsive to said first digital x-ray picture data for displaying said x-ray picture taken prior to injection of the contrast medium;

second display means responsive to said second digital x-ray picture data for displaying said x-ray picture taken after injection of the contrast medium;

processor means for operating on a predetermined number of frames of said first and second digital x-ray picture data to develop first and second processed picture data, respectively, and for subtractively combining said first and second processed picture data to produce picture data corresponding to said pictorial representation of the differences between said successive x-ray pictures taken of the subject prior to and after injection of the contrast medium;

third storage means for storing said picture data corresponding to said pictorial representation of the differences between said successive x-ray pictures taken of the subject prior to and after injection of the contrast medium; and third display means responsive to said picture data stored in said third storage means for displaying said pictorial representation of the differences between said successive x-ray pictures taken of the subject prior to and after injection of the contrast medium.

18. The system of claim 17, wherein said processor means enhances said picture data stored in said third storage means to obtain enhanced picture data corresponding to said pictorial representation of the differences between said successive x-ray picture taken of the subject prior to and after injection of the contrast medium, said system further comprising fourth storage means for storing said enhanced picture data, and fourth display means responsive to said enhanced picture data for displaying an enhanced version of said pictorial representation of the differences between said successive x-ray pictures taken of the subject prior to and after injection of the contrast medium.

19. The system of claim 17, wherein said processor means averages at least one of said first and second digital x-ray picture data.

20. The system of claim 17, wherein said processor means enhances at least one of said first and second digital x-ray picture data.

21. The system of claim 17, wherein said processor means convolves said first digital x-ray picture data.

* * * * *